Figure 1:
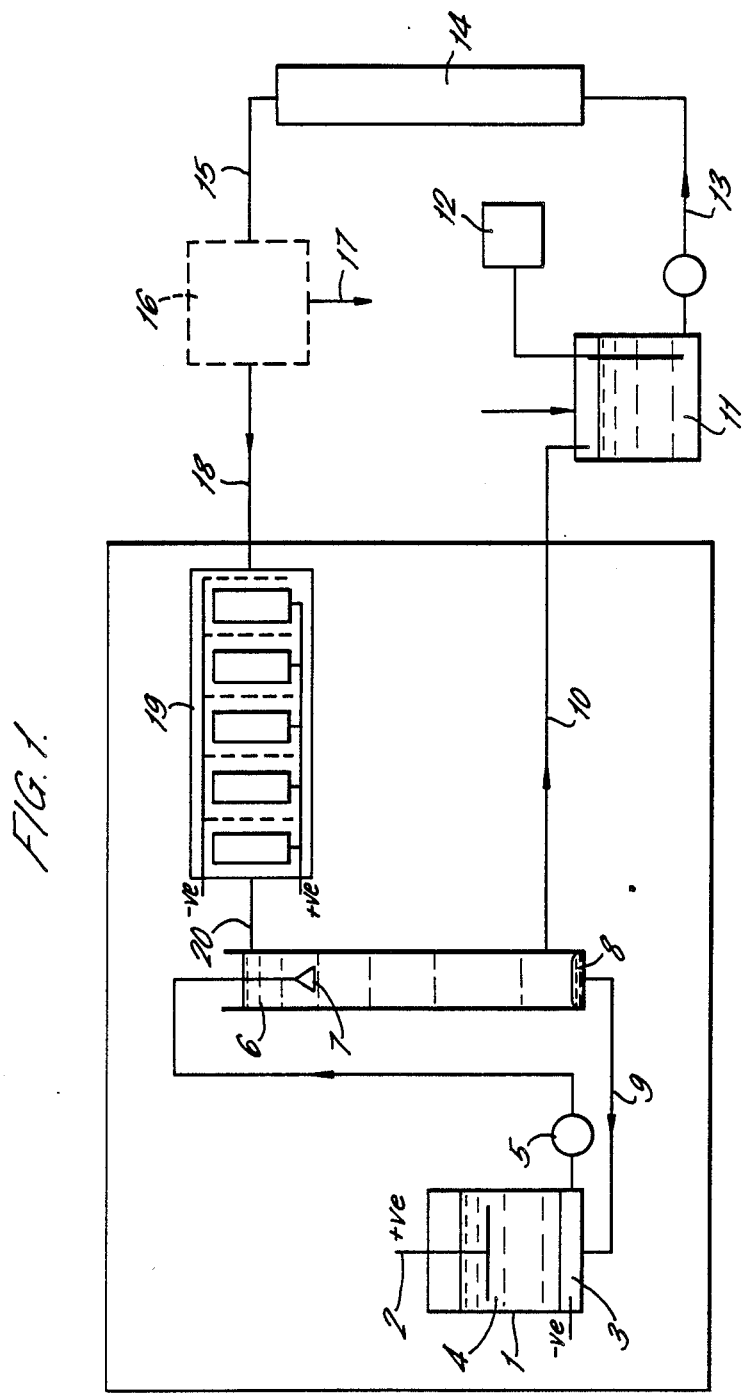

United States Patent [19]

Drakesmith

[11] Patent Number: 4,973,550
[45] Date of Patent: Nov. 27, 1990

[54] PROCESS FOR THE ELECTROCHEMICAL REGENERATION OF CO-ENZYMES

[75] Inventor: Frederick G. Drakesmith, Clwyd, Wales

[73] Assignee: The Electricity Council, London, England

[21] Appl. No.: 128,354

[22] Filed: Dec. 3, 1987

[30] Foreign Application Priority Data

Dec. 8, 1986 [GB] United Kingdom ............... 8629297

[51] Int. Cl.$^5$ .................... C12Q 1/54; C12N 11/14
[52] U.S. Cl. ................................... 435/41; 435/26; 435/288; 204/219; 204/220; 204/402
[58] Field of Search ............... 435/26, 288, 280, 174, 435/183, 189, 190, 175, 161, 41; 204/131, 402, 220

[56] References Cited

U.S. PATENT DOCUMENTS

4,490,464 12/1984 Gorton et al. .................... 435/4

FOREIGN PATENT DOCUMENTS

5513072 1/1980 Japan .
2033428 5/1980 United Kingdom .

OTHER PUBLICATIONS

Aizawa et al., Chemical Abstracts, vol. 82, No. 25, Jun. 23, 1975, p. 182, #166519U.
Aizawa et al., Chemical Abstracts, vol. 84, No. 17, Apr. 26, 1976, p. 201, p. 201, #117673X.
Aizawa et al., Chemical Abstracts, vol. 86, No. 3, Jan. 17, 1977, p. 114, #12838T.
Aizawa et al., Chemical Abstracts, vol. 86, No. 20, May 16, 1977, p. 516, #147648B.
Wandry et al., "Coenzyme Regeneration in Membrane Reactors", Enzymes and Immobilized Cells in Biotech., 1985, pp. 177–209.
Simon et al., "Electro-Enzymatic and Electro-Microbial Stereospecific Reductions", Angen. Chem. Int. Ed. Engl., 20, No. 10, 1981.
Blaedel et al., "Study of the Electrochemical Oxidation of Reduced Nicotinamide Adenine Dinucleotide", Analytical Chemistry, vol. 47, 1975, pp. 1337–1343.
DiCosimo et al., "Enzyme-Catalyzed Organic Synthesis", J. Org. Chem. 45(22), 1981, pp. 4622–4623.

Primary Examiner—Robert A. Wax
Assistant Examiner—Janelle D. Waack
Attorney, Agent, or Firm—Beveridge, DeGrandi & Weilacher

[57] ABSTRACT

A process for the electrochemical regeneration of a co-enzyme, which process comprises the steps of
(i) electrochemically oxidizing a medium containing oxidized co-enzyme and biochemically inactive isomers of the co-enzyme to oxidize the biochemically inactive isomers,
(ii) generating a mercury amalgam in an electrochemical cell;
(iii) contacting in a reaction vessel the mercury amalgam and the medium containing the oxidize co-enzyme from step (i), with one of the reactants selected from the mercury amalgam and the oxidized co-enzyme being in the form of a plurality of droplets.

18 Claims, 2 Drawing Sheets

PROCESS FOR THE ELECTROCHEMICAL REGENERATION OF CO-ENZYMES

The present invention relates to a process for the electrochemical regeneration of co-enzymes and the application of this technique to the synthesis of organic chemicals.

Living organisms perform extensive and complex chemical changes within their cell structures. These operations occur under normal conditions of temperature and pressure, and at moderate pH values. This is only possible because of the moderating effect of proteinaceous catalysts present in the organisms which are called enzymes. Enzymes are classified by the type of reaction which they assist in bringing about, e.g. oxido-reductases, transferases, hydrolases, isomerases, etc. The driving force for these reactions in the living cell is ultimately derived from the foodstuff consumed by the living organism, but eventually, as it is transmitted down the chain, the "energy currency" becomes, in the case of oxido-reductase reactions, the co-enzymes, e.g. nicotinamide adenine dinucleotide (AND+), flavine adenine dinucleotide (FAD+), nicotinamide adenine dinucleotide phosphate (NADP+), etc. If it were possible to control the redox reactions of these co-enzymes and so regenerate them artificially using electrochemical techniques then it should be possible to drive any particular enzyme catalysed reaction at a much enhanced rate, independent of the kinetics of the preceding bio-reactions, and in either a forwards or backwards direction. Because of the mild conditions and known specificity of enzyme catalysed reactions, a synthetic process based on this bio-electrochemistry would be particularly suitable for the production of speciality and fine chemicals and pharmaceuticals which commonly required the modification of a single functional group, whilst retaining the rest of the often labile molecule intact. The problem hitherto has been adequately to mimic nature in the reversibility of utilisation of the co-enzyme couple.

In vivo, AND+ and NADH are generated for use in any particular reaction via the preceding enzymic reaction, and, because of the exact stereo-specific and thermodynamic matching of a reaction within the 3-dimensional structure of the enzyme molecule the yield and conversion of AND+ to NADH (or vice-versa) is 100% of the desired 1,4-isomer.

However, artificial methods of conversion of the AND+/NADH redox couple can damage the delicate and complex co-enzyme, or produce dimers and isomers other than the desired 1,4- form. This is because, very often, the precise energy match is not supplied, and also because the stereo-specific constraints of the enzyme molecule are not present to control the reaction when it is conducted either in solution or on an electrode surface.

We have now developed a method for artificially regenerating co-enzymes by electrochemical techniques which overcomes these problems.

Accordingly, the present invention provides a process for the electrochemical regeneration of a co-enzyme, which process comprises the steps of (i) electrochemically oxidising a solution or emulsion containing oxidised co-enzyme and biochemically inactive isomers of the co-enzyme to oxidise the biochemically inactive isomers, (ii) generating a mercury amalgam in an electrochemical cell;

(iii) contacting in a reaction vessel the mercury amalgam and the solution or emulsion of the oxidised co-enzyme from step (i), either the amalgam or the oxidised co-enzyme being in the form of a plurality of droplets.

The solution or emulsion containing the oxidised co-enzyme and biochemically inactive isomers of the co-enzyme may be the solution or emulsion from an enzyme reactor containing an immobilized oxido-reductase, e.g. alcohol dehydrogenase, malate dehydrogenase, etc., optionally after separation of the product produced by the enzyme reaction therefrom. It will be understood that the product will be required to be separated from the solution if it is sensitive to the conditions in steps (i) and (iii) of the process of the invention.

In the electrochemical oxidiser biochemically inactive isomers of the co-enzyme are oxidised to the active oxidised form of the co-enzyme. For example inactive 1,6- and 1,2- dihydroisomers of NADH are electrochemically oxidised to AND+. The AND+ solution is then reduced to NADH according to the process of the invention and a mixture of NADH isomers is formed (approximately 70% 1,4- , 27% 1,2- and 3% 1,6-dihydro) using the amalgam spray reducer. It will be understood that any electrochemical cell can be used in which the required oxidation reaction can be carried out.

In carrying out the process of the present invention the amalgam is preferably an amalgam of lithium, sodium or potassium, although other metal amalgams which have a sufficiently high reduction potential may also be used. The reaction vessel is preferably in the form of a cylinder. The cylinder preferably has a length in the range of from 10cm to 2.5m when the amalgam is in the form of a plurality of droplets and a length of from 2 to 100 centimeters when the the oxidised co-enzyme is in the form of a plurality of droplets.

When the reactant droplets are of the mercury amalgam they are preferably introduced to the top of a vertical reaction vessel and the solution or emulsion of the oxidised co-enzyme is preferably passed counter-currently through the reaction vessel. The partially depleted mercury amalgam is preferably collected and returned to the electrochemical cell. When the reaction vessel is vertical, then the partially depleted mercury amalgam may be returned to the electrochemical cell under gravity. The mercury amalgam should not be allowed to become fully depleted of the other metal, since the mercury would then denature the enzyme. The solution or emulsion of the oxidised co-enzyme is removed from the reaction vessel.

When the reactant droplets are of the oxidised co-enzyme they are preferably introduced to the bottom of a vertical reaction vessel and the mercury amalgam is preferably passed co-currently through the reaction vessel. The deleted mercury amalgam is preferably collected and returned to the electrochemical cell under gravity. The solution or emulsion of the oxidised co-enzyme is removed from the reaction vessel.

The principal parameters controlling the extent of the reduction reaction are:

(a) the reduction potential of the amalgam, which is governed by the nature of the metal in solution, for example lithium, sodium or potassium, and by the concentration of the metal which is determined by the current in the electrochemical amalgam cell and the rate of passage of the amalgam from the amalgam generating electrochemical cell through tHe reaction vessel and back to the electrochemical cell;

(b) the surface area of the reactant droplets;

(c) the concentration of the oxidised co-enzyme in the solution or emulsion;

(d) the composition of the solution or emulsion, i.e. the pH and the presence of any buffering ions;

(e) the contact time of the amalgam with the oxidised co-enzyme which is determined by the length and aspect ratio of the reaction vessel and the rates of passage of the amalgam and the solution or emulsion of the oxidised co-enzyme through the reaction vessel; and (f) the temperature.

The present invention also provides a method of carrying out an enzymatic reduction reaction which method comprises (a) contacting in an enzyme reactor a solution or emulsion of a reduced co-enzyme and a solution or emulsion of the compound to be reduced with an oxidoreductase enzyme;

(b) removing from the enzyme reactor the solution or emulsion containing the reduced product, biochemically inactive isomers of the co-enzyme and oxidised co-enzyme, and optionally separating the product therefrom;

(c) electrochemically oxidising the solution or emulsion from step (b) to oxidise the biochemically inactive isomers;

(d) generating a mercury amalgam in an electrochemical cell;

(e) contacting in a reaction vessel the mercury amalgam from step (d) and the solution or emulsion of the oxidised co-enzyme from step (c). Either the amalgam or the oxidised co-enzyme being in the form of a plurality of droplets.

The oxido-reductase contained in the enzyme reactor is preferably immobilized on a support. Examples of oxido-reductases are alcohol dehydrogenase and malate dehydrogenase.

The compound which may be reduced enzymatically according to the above method may be, for example, acetaldehyde, octanal or oxaloacetic acid. The solution which emerges from the enzyme reactor contains the reduced product, for example, ethanol, octanol or malic acid, together with the oxidised co-enzyme and any unreacted isomers of the co-enzyme.

The solution which emerges from the enzyme reactor may be treated in order to remove the product therefrom. This may be accomplished by passing the solution through a separator. Alternatively, this step may be omitted if the product is electrochemically stable and the total solution emerging from the enzyme reactor may be subjected to the electrochemical oxidation. In the electrochemical oxidation step any inactive isomers of the co-enzyme, e.g. the 1,6- and 1,2-dihydroisomers of NADH, are electrochemically oxidised. The oxidised co-enzyme is then converted into its reduced form in the amalgam reaction vessel in the manner as hereinbefore described.

It will be appreciated that the co-enzyme will generally be present in an aqueous buffered solution at a pH in the range of from 8 to 12.

It will be understood that the method as hereinbefore described may be carried out continuously or semi-continuously. A crucial factor in the ability to carry out the method in this manner is the longevity of the co-enzyme, i.e. the number of cycles a particular co-enzyme can perform before it loses its activity. The principal parameters controlling the extent of these reactions, both desired and undesired, have been discussed above.

The present invention also includes within its scope apparatus for carrying out an enzymatic reduction reaction which comprises:

(i) an enzyme reactor containing an immobilized oxido-reductase enzyme having an inlet for the introduction of a solution or emulsion of the product to be reduced and a solution or an emulsion of a reduced co-enzyme, or a mixture thereof, and an outlet for the removal from the enzyme reactor of a solution or emulsion containing the reduced product, biochemically inactive isomers of the co-enzyme and oxidised co-enzyme;

(ii) an optional separator for separating the reduced product from the solution or emulsion removed from the enzyme reactor;

(iii) an electrochemical oxidation cell for the oxidation of the solution or emulsion of the co-enzyme removed from the enzyme reactor;

(iv) an electrochemical cell for the generation of a mercury amalgam having an anode, a mercury cathode and an electrolyte comprising a metal hydroxide solution;

(v) a reaction vessel having means for the production of droplets of the mercury amalgam or the solution or emulsion of the co-enzyme and an inlet and an outlet for the passage of the other reactant therethrough;

(vi) means for the passage of the mercury amalgam from the electrochemical cell to the reaction vessel;

(viii) means for the passage of the depleted mercury amalgam from the reaction vessel to the electrochemical cell; and (viii) means for the passage of the reduced co-enzyme back to the enzyme reactor (i).

Figure 2:
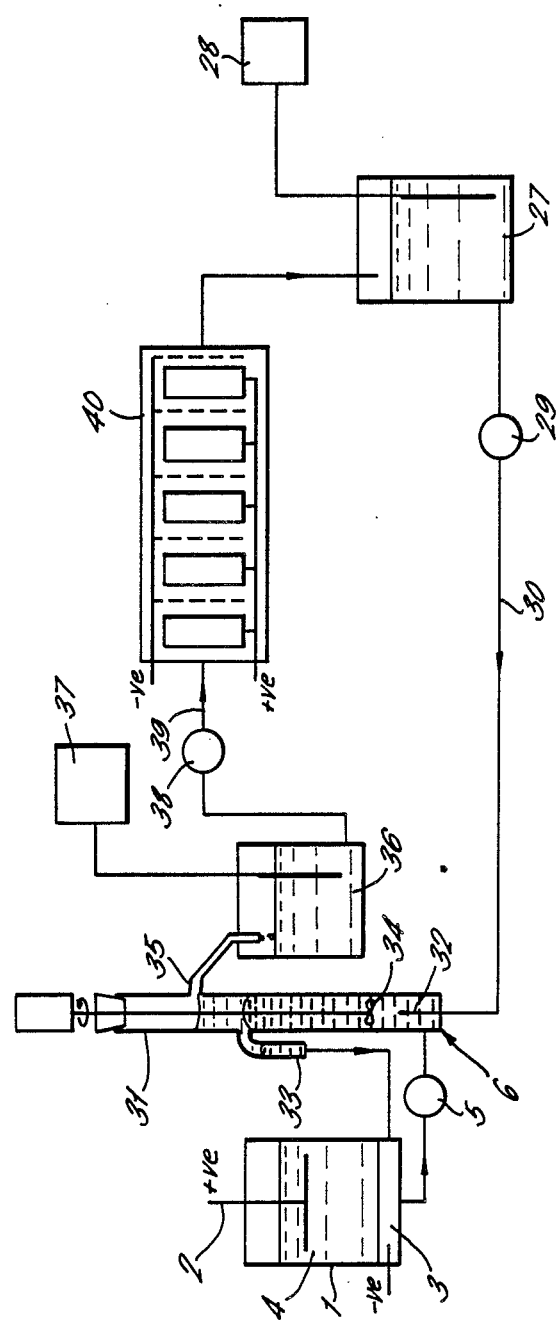

The present invention will be further described with reference to the accompanying drawings, in which:

FIG. 1 illustrates the method of the present invention for carrying out enzymatic reactions; and FIG. 2 illustrates the process of the present invention for the regeneration of co-enzymes:

Referring to FIG. 1 an amalgam generator 1 comprises an electrochemical cell having a nickel anode 2 and a mercury cathode 3. For the production of a potassium amalgam the electrochemical cell contains a solution 4 of potassium hydroxide. The electrochemical cell is connected via a pump 5 to the head of a reaction column 6. The mercury amalgam is thus pumped from the electrochemical cell to the reaction vessel where it emerges as a fine spray through a porous glass frit 7 positioned at the top of the reaction vessel. The potassium depleted mercury is collected at the bottom 8 of the reaction vessel and returned via line 9 to the electrochemical cell under gravity. The cycle can then begin again.

In the arrangement shown in FIG. 1, a solution or emulsion of reduced co-enzyme, e.g. NADH, leaves the bottom 8 of reactor 6 via line 10. It is then passed to a reservoir 11 fitted with a pH controller 12 and mixed with a solution or emulsion of the product which is to be reduced. The mixture is then pumped along line 13 to an enzyme reactor 14 containing an immobilized oxido-reductase. The desired enzymatic reaction takes place in the enzyme reactor 14 and the solution or emulsion emerging from the enzyme reactor along line 15 contains the reduced product, oxidised co-enzyme and biochemically inactive isomers of the co-enzyme. The product may, if desired or if necessary, be separated from the solution or emulsion in separator 16 and removed along line 17. The remaining solution is then passed along line 18 to an oxidiser cell 19 where the biochemically inactive isomers are oxidised. The solution or emulsion containing the oxidised co-enzyme, e.g. $NAD^+$ is then passed along line 20 to the top of the amalgam reactor 6 where it is subjected to reduction by mercury amalgam droplets. The reduced product, e.g. NADH, leaves reactor 6 along line 10 as described hereinbefore.

In the arrangement shown in FIG. 2, a solution or emulsion of oxidized co-enzyme is contained in reservoir 27 fitted with a pH controller 28. The emulsion or solution of the oxidised co-enzyme is then pumped by pump 29 along line 30 to the bottom of the reactor 6 where it is introduced into reaction vessel 31 as a plurality of fine droplets through a vertical sparge pipe 32. The reaction vessel 31 is filled with a column of mercury amalgam generated in an amalgam generator 1 as described with reference to FIG. 1. The mercury amalgam is pumped to the bottom of the amalgam reducer 31 by means of a pump 5. The mercury amalgam fills the reaction vessel 31 up to the level of the overflow 33 via which the amalgam is returned to the bottom of amalgam generator 1. The reaction vessel 31 is fitted with a paddle stirrer 34 to ensure thorough mixing of the amalgam with the oxidised co-enzyme. The solution or emulsion containing the reduced co-enzyme is removed from the reaction vessel 31 via outlet 35 which is positioned at a higher level on the reaction vessel than the amalgam outlet 33. The solution or emulsion of the reduced co-enzyme is then passed to reservoir 36 which is fitted with a pH controller 37. The solution or emulsion of the reduced co-enzyme is then pumped by pump 38 from reservoir 36 along line 39 to oxidiser cell 40 where it is oxidised. It is then passed to the reservoir 27.

The oxidiser cells 19 and 40 which are shown schematically in FIGS. 1 and 2, respectively, consist of a series of axial flow cells clamped together in a multistage arrangement. Each cell is fitted with nickel electrodes, the cathodes being made from expanded nickel and the anodes from nickel foam to ensure that a maximum surface area is presented to the co-enzyme. The cell is designed so that the solution passes through the electrodes, thus providing intimate contact and agitation. The cells are electrochemically connected in parallel, with voltage control, so that oxidation of the desired electro-active species, and no other, occurs.

The present invention will be further described with reference to the following Examples.

EXAMPLE 1

Reducer and Oxidiser Combined

An amalgam reducer and electrochemical oxidiser were combined as shown in FIG. 2 and the system circulated in a closed loop operation. Samples were withdrawn from various points in the loop and analysed for co-enzyme concentration and activity. In this way the performance of each component as well as the "total module" could be assessed.

A mercury amalgam was generated in the amalgam cell by passing a 10a current through potassium hydroxide solution (10M) using a nickel disc anode and a mercury cathode. The amalgam was pumped at a rate of 100 ml min$^{-1}$ from the amalgam generator to the amalgam reducer. The amalgam reducer had a diameter of 1.8 cm and a mercury column height of 25.0 cm. The system volume was approx. 700 ml and the $NAD^+$ concentration 1.0% w/w in a 0.5M $K_4P_2O_7$ buffer solution. The pH of the reservoir solution before the reducer was continuously modified to pH 10, and that before the oxidiser cell to pH 9, using 10M KOH solution and conc.$H_3PO_4$ respectively.

The flow rate of the aqueous co-enzyme solution was controlled at 100 ml min$^{-1}$ through the system. The oxidiser cell was voltage controlled to give a current of between 3a and 4a.

Table I illustrates the level of damage to the co-enzyme as a function of time at the points before reducer (BR), after reducer (AR), before oxidiser (BO) and after oxidiser (AO).

TABLE I

| Time minutes | Damage (% of original co-enzyme) | | | | | |
|---|---|---|---|---|---|---|
| | BR | AR | AR Corrected | BO | AO | AO Corrected |
| 1 | 1.4 | 16.2 | | 10.3 | 0 | |
| 2 | 2.9 | 2.9 | | 8.8 | 7.3 | |
| 3 | 4.4 | 4.4 | | 7.4 | 1.4 | |
| 4 | 4.4 | 4.4 | 3.6 | 7.4 | 0 | — |
| 6 | 5.9 | 5.9 | 4.5 | 7.4 | 4.4 | 3.0 |
| 8 | 8.8 | 8.8 | 7.0 | 10.3 | 5.9 | 4.0 |
| 10 | 8.8 | 10.3 | 8.3 | 13.2 | 10.3 | 8.3 |
| 15 | 10.3 | 11.7 | 8.5 | 13.2 | 10.3 | 7.0 |
| 39 | — | 16.2 | 10.7 | — | 20.6 | 15.4 |
| 60 | — | 30.9 | 21.1 | — | 41.2 | 32.9 |
| 120 | — | 58.8 | 45.7 | — | 63.2 | 53.2 |

As can be seen from these data this small scale rig was capable of processing 60g of coenzyme per hour with a damage rate of approximately 0.4% min$^{-1}$, i.e. 99.6% of the co-enzyme being processed per minute was successfully passing through the regeneration cycle.

EXAMPLE 2

Bioelectrochemical Reduction of Acetaldehyde - Full System

The system was set up as illustrated in FIG. 1, with the reaction parameters set out below. Acetaldehyde was added stoichemtrically and continuously to the mixing vessel, and was converted to ethanol in the enzyme reactor packed with immobilised alcohol dehydrogenase. The pH was maintained at 7.0 by means of an automatic pH controller. Performance characteristics for each module at various times are given below in Table 3.

TABLE 2

| Closed cycle reaction with immobilised enzyme | |
|---|---|
| Total vol. 750 ml, 0.1% NAD, pH 7 | |
| Pumping rate 9 mls min$^{-1}$ | |
| Current 100/800 mA (amalgam cell) 5/25 mA (oxidiser cell) | |
| At time 55 mins conversion in enzyme cell | = 20% |
| At time 55 mins conversion in oxidiser cell | = 23% |
| At time 55 mins conversion in reducer | = 43% |
| At time 90 mins conversion in enzyme cell | = 19% |
| At time 90 mins conversion in oxidiser cell | = 17% |
| At time 90 mins conversion in reducer cell | = 36% |
| At time 120 mins conversion in enzyme cell | = 17% |
| At time 120 mins conversion in oxidiser | = 6.6% |
| At time 120 mins conversion in reducer cell | = 24% |
| At time 150 mins conversion in enzyme | = 17% |
| At time 150 mins conversion in oxidiser | = 11% |
| At time 150 mins conversion in reducer | = 29% |
| The conversion was expressed in terms of % of total co-enzyme present. | |

Immobilisation of Alcohol Dehydrogenase

The alcohol dehydrogenase used in above experiment was immobilised as follows. Fluorsil (60/100 mesh, 10 g) was covered with a 10% aqueous solution of 3-amino-propyltrimethoxysilane at pH 2.0 (pH adjusted with phosphoric acid) and left for 4 hours. The supernatant liquor was then decanted and the material washed by repeated addition and decanting of aliquots of water. When clear, the material was filtered, washed with water, and transferred to a Petri dish and dried in an oven at 120° overnight. After cooling the material was handled in sterlised glassware (i.e. rinsed in 1% sodium metabisulphate solution) and covered with 2.5% glutaraldehyde solution prepared is 0.3M $K_4P_2O_7$ buffer at pH 7.5. This was left to stand for 4 hours with occasional stirring, and then rinsed with $K_4P_2O_7$ buffer solution at pH 7.5. After draining, using a filter funnel, the solid was placed in a sterilised beaker and covered with 20 ml 0.3M $K_4P_2O_7$ buffer solution (pH7.5) containing 10 mg/ml alcohol dehydrogenase (i.e. 200mg ADH) and allowed to stand for 2 days. The immobilised enzyme was then washed, filtered, and rinsed with buffer solution before being used in the enzyme reactor. After use the immobilised enzyme was stored in 1% sodium metabisulphate solution in $K_4P_2O_7$ (pH7.5) buffer solution under refrigeration.

EXAMPLE 3

Bioelectrochemical Reduction of Acetaldehyde

The system was set up as illustrated in FIG. 1. $NAD^+$ (0.1% w/w) in an aqueous buffered solution (750 ml, pH 8, 0.1M potassium pryrophosphate+KOH (soln) was passed through the amalgam spray reaction column with a counter current of potassium amalgam, produced in an amalgam generator cell (900 ma, 10 M KOH soln). The emerging NADM solution was pumped into the enzyme reactor, containing immobilised alcohol dehydrogenase, and to which acetaldehyde was added stoichiometrically and continuously. The solution from the enzyme reactor was then passed through the oxidiser cell (100ma), where any NADH was re-oxidised back to $NAD^+$ and returned to the reservoir to begin another cycle. Samples were withdrawn from various points around the system and analysed in the usual manner, for co-enzyme concentration and activity. Typical results are given below in Table 2.

TABLE 3

| | |
|---|---|
| At $T_{20}$ conversion in enzyme cell | = 17% |
| At $T_{20}$ conversion in oxidiser | = 20% |
| At $T_{20}$ conversion in reducer | = 37% |
| At $T_{30}$ conversion in enzyme cell | = 13% |
| At $T_{30}$ conversion in oxidiser | = 20% |
| At $T_{30}$ conversion in reducer | = 33% |
| At $T_{50}$ conversion in enzyme cell | = 13% |
| At $T_{50}$ conversion in oxidiser | = 9% |
| At $T_{50}$ conversion in reducer | = 23% |

EXAMPLE 4

An aqueous solution of $NAD^+$ (1.0%, pH 10) was injected into the base of a column of regenerated potassium amalgam (I=1500 ma) immediately below a high speed stirrer to ensure intimate contact. Proper regulation of potassium concentration, pH, column depth, stirrer speed and contact times controlled the rate of reduction of $NAD^+$ to NADH, and the amount of damage incurred. Typical experimental results are given below:

| $NAD^+$ Volume Passed (ml) | Monitored pH | Conversion (%) | Active NADH prod. (%) | Damage % |
|---|---|---|---|---|
| 50 | 12.15 | 100 | 63.6 | 0 |
| 100 | 12.12 | 100 | 63.6 | 0 |
| 200 | 12.09 | 100 | 65.8 | 0 |
| 300 | 12.17 | 100 | 65.8 | 0 |
| 400 | 12.07 | 100 | 65.8 | 0 |
| 480 | 12.04 | 100 | 65.8 | 0 |

I claim:

1. A process for the electrochemical regeneration of a co-enzyme, which process comprises the steps of
   (i) electrochemically oxidising a medium containing oxidised co-enzyme and biochemically inactive isomers of the co-enzyme to oxidise the biochemically inactive isomers,
   (ii) generating a mercury amalgam in an electrochemical cell;
   (iii) contacting in a reaction vessel the mercury amalgam and the medium containing the oxidised co-enzyme from step (i), with one of the reactants selected from the mercury amalgam and the oxidised co-enzyme being in the form of a plurality of droplets.

2. Process according to claim 1 wherein the medium containing oxidised co-enzyme and biochemically inactive isomers of the co-enzyme is obtained from an enzyme reactor containing an immobilized oxido-reductase, optionally after the separation of the product produced by the enzyme reaction therefrom.

3. Process according to claim 1 wherein the mercury amalgam is selected from the group consisting of lithium, sodium and potassium amalgams.

4. Process according to claim 1 wherein the mercury amalgam is reacted in the form of droplets and the reaction vessel is in the form of a cylinder having a length in the range of from 10cm to 2.5 meters.

5. Process according to claim 1 wherein the oxidised co-enzyme is reacted in the form of droplets and the reaction vessel is in the form of a cylinder having a length in the range of from 2 to 100 centimeters.

6. Process according to claim 1 wherein the oxidised co-enzyme is present in an aqueous solution.

7. Process according to claim 1 wherein the oxidised co-enzyme is present in solution in an organic solvent.

8. Process according to claim 1 wherein droplets of the mercury amalgam are introduced to the top of a vertical reaction vessel and the medium containing the oxidised co-enzyme is passed counter-currently through the reaction vessel.

9. Process according to claim 1 wherein droplets of the medium containing the oxidised co-enzyme are introduced to the bottom of a vertical reaction vessel and the mercury amalgam is passed co-currently through the reaction vessel.

10. Process according to claim 1 wherein the partially depleted mercury amalgam is collected and returned to the electrochemical analgam generating cell.

11. A method of carrying out an enzymatic reduction reaction which method comprises
   (a) contacting in an enzyme reactor a medium containing a reduced co-enzyme and a medium containing the compound to be reduced with an oxidoreductase enzyme:

(b) removing from the enzyme reactor the medium containing the reduced product, biochemically inactive isomers of the co-enzyme and oxidised co-enzyme, and optionally separating the product therefrom;

(c) electrochemically oxidising the medium from step (b) to oxidise the biochemically inactive isomers;

(d) generating a mercury amalgam in an electrochemical cell;

(e) contacting in a reaction vessel the mercury amalgam from step (d) and the medium containing the oxidised co-enzyme from step (c), with one of the reactants from the mercury amalgam and the oxidised co-enzyme being in the form of a plurality of droplets.

12. Method according to claim 11 wherein the oxidoreductase contained in the enzyme reactor is immobilized on a support.

13. Method according to claim 11 wherein the oxidoreductase is alcohol dehydrogenase or malate dehydrogenase.

14. Method according to claim 11 wherein the compound to be reduced in selected from the group consisting of acetaldehyde, octanal and oxaloacetic acid.

15. Method according to claim 11 wherein the co-enzyme is dihydro nicotinamide adenine dinucleotide (NADH).

16. Method according to claim 11 wherein the medium emerging from the enzyme reactor is passed through a separator to remove the produce therefrom.

17. Method according to claim 11 which is carried out in a manner selected from continuous and semicontinuous operation.

18. Apparatus for carrying out an enzymatic reduction reaction which comprises:

(i) an enzyme reactor containing an immobilized oxido-reductase enzyme having an inlet for the introduction of a medium containing the product to be reduced and an medium containing a reduced co-enzyme, and an outlet for the removal from the enzyme reactor of a medium containing the reduced product, biochemically inactive isomers of the co-enzyme and oxidised co-enzyme;

(ii) an optional separator for separating the reduced product from the medium removed from the enzyme reactor;

(iii) an electrochemical oxidation cell for the oxidation of the medium containing the co-enzyme removed from the enzyme reactor;

(iv) an electrochemical cell for the generation of a mercury amalgam having an anode, a mercury cathode and an electrolyte comprising a metal hydroxide solution;

(v) a reaction vessel having means for the production of droplets selected from the group consisting of the mercury amalgam and the medium containing the co-enzyme and an inlet and an outlet for the passage of the other reactant therethrough;

(vi) means for the passage of the mercury amalgam from the electrochemical cell to the reaction vessel;

(viii) means for the passage of the depleted mercury amalgam from the reaction vessel to the electrochemical cell; and (viii) means for the passage of the reduced co-enzyme back to the enzyme reactor (i).

* * * * *